United States Patent
Wang et al.

(10) Patent No.: US 10,233,137 B1
(45) Date of Patent: Mar. 19, 2019

(54) METHOD FOR REMOVING UNSATURATED HALOGENATED IMPURITIES FROM 2,3,3,3-TETRAFLUOROPROPENE (HFO-1234YF)

(71) Applicant: Honeywell International Inc., Morris Plains, NJ (US)

(72) Inventors: Haiyou Wang, Amherst, NY (US); Terris Yang, East Amherst, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/783,401

(22) Filed: Oct. 13, 2017

(51) Int. Cl.
*C07C 17/395* (2006.01)

(52) U.S. Cl.
CPC ................... *C07C 17/395* (2013.01)

(58) Field of Classification Search
CPC ....... C07C 17/395; C07C 17/04; C07C 21/18; C07C 19/07
See application file for complete search history.

(56) References Cited

U.S. PATENT DOCUMENTS

| | | |
|---|---|---|
| 8,058,486 B2 | 11/2011 | Merkel et al. |
| 8,766,020 B2 | 7/2014 | Wang et al. |
| 2012/0184785 A1 | 7/2012 | Cottrell et al. |

FOREIGN PATENT DOCUMENTS

| | | |
|---|---|---|
| GB | 2547277 A | 8/2017 |
| WO | 2017013405 A1 | 1/2017 |

OTHER PUBLICATIONS

U.S. Appl. No. 62/416,206, filed Nov. 2, 2016, 17 pages.

*Primary Examiner* — Jafar F Parsa
(74) *Attorney, Agent, or Firm* — Faegre Baker Daniels LLP

(57) ABSTRACT

A method for removing unsaturated halogen impurities from 2,3,3,3-tetrafluoropropene (HFO-1234yf) of the type that may otherwise be difficult to separate from HFO-1234yf due to the impurities having boiling points which are close to that of HFO-1234yf and/or the potential of one or more of the impurities to form azeotropic mixtures with HFO-1234yf. A HFO-1234yf stream including unsaturated halogenated impurities is first passed through a caustic scrubber and is then passed through an acid scrubber. In the caustic scrubber and acidic scrubber, undesirable impurities are removed, in particular, 3,3,3-trifluoropropene (1243zf), 1-chloro-1-fluoroethylene (1131a), vinyl chloride (1140), and/or 1-chloro-2-fluoroethylene (1131).

17 Claims, 1 Drawing Sheet

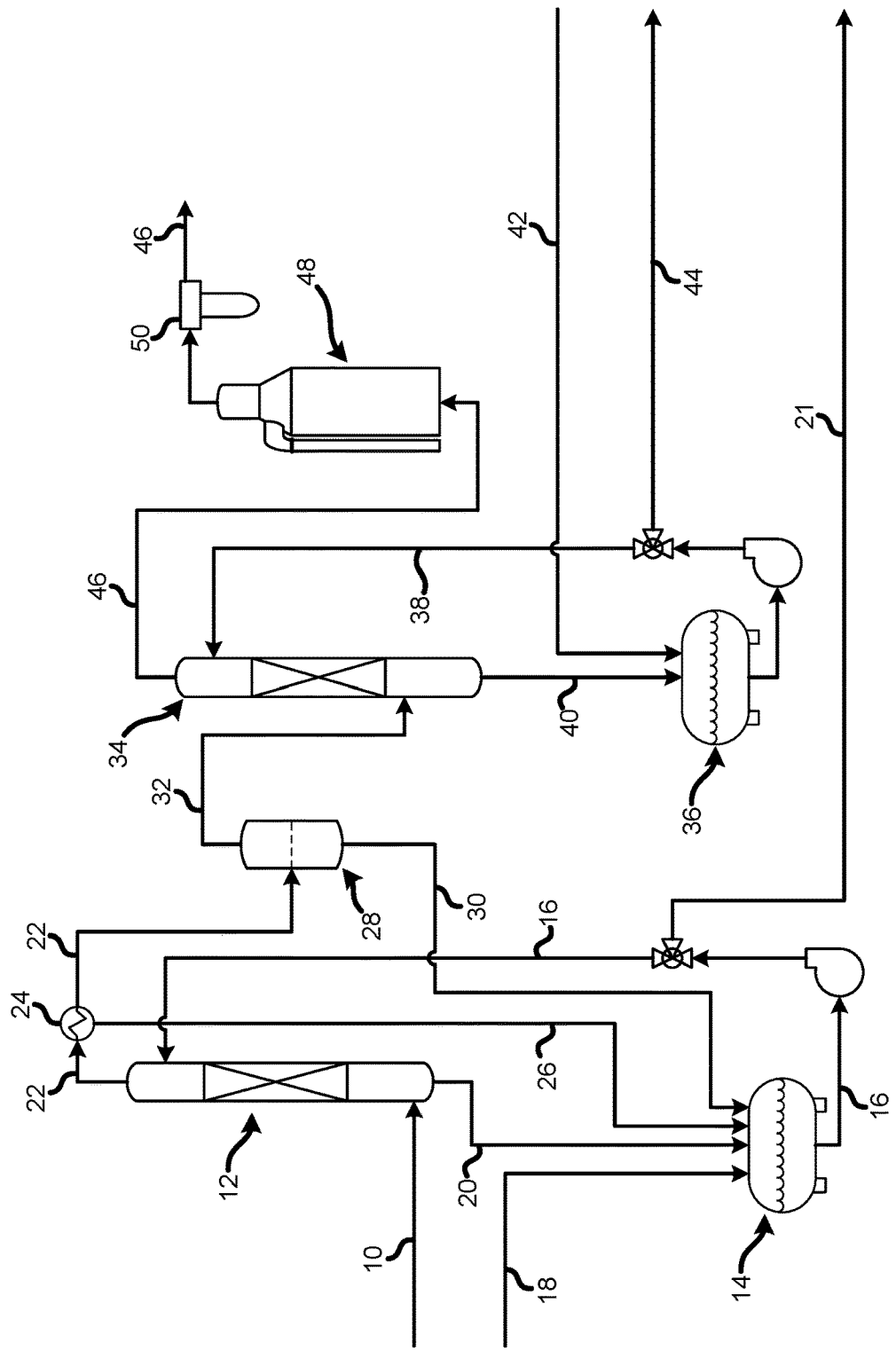

METHOD FOR REMOVING UNSATURATED HALOGENATED IMPURITIES FROM 2,3,3,3-TETRAFLUOROPROPENE (HFO-1234YF)

BACKGROUND

1. Field of the Disclosure

The present disclosure provides a method for removing unsaturated halogenated impurities from 2,3,3,3-tetrafluoropropene (HFO-1234yf).

2. Description of the Related Art

Chlorine-containing compounds, such as chlorofluorocarbons (CFCs), have been employed as refrigerants, foam blowing agents, cleaning agents, solvents, heat transfer media, sterilants, aerosol propellants, dielectrics, fire extinguishing agents, and power cycle working fluids. Such chlorine-containing compounds have proven to be detrimental to the Earth's ozone layer. Many of the hydrofluorocarbons (HFCs), used as the substitutes of CFCs, have been found to contribute to global warming. For these reasons, there is a worldwide effort to develop new compounds that are more environmentally benign while at the same time being as effective, or more effective, from a performance standpoint.

Compositions containing fluorinated olefins, including particularly 2,3,3,3-tetrafluoropropene (HFO-1234yf, or 1234yf), are among the materials being developed for use in the aforementioned applications. In addition, HFO-1234yf can be used as a feedstock monomer for synthesis of fluoropolymers and macromolecular compounds.

Methods for the production of 1234yf are known. In one method, disclosed in U.S. Pat. No. 8,058,486, which is expressly incorporated herein by reference, 1,1,2,3-tetrachloropropene (1230xa) is fluorinated with hydrogen fluoride to produce 2-chloro-3,3,3-trifluoropropene (1233xf), followed by reacting the 1233xf with hydrogen fluoride to produce 2-chloro-1,1,1,2-tetrafluoropropane (244bb). In the final step, the 244bb is dehydrochlorinated to produce 1234yf. This 3-step process is set forth below:

Step (1) 1230xa+3HF→2-chloro-3,3,3-trifluoropropene (1233xf)+3HCl in a vapor phase reactor charged with a solid catalyst;

Step (2) 1233xf+HF→2-chloro-1,1,1,2-tetrafluoropropane (244bb) in a liquid phase reactor charged with a liquid catalyst; and Step (3) 244bb→1234yf+HCl in a vapor phase reactor.

It has been found that certain unsaturated halogenated impurities may be present in the 1234yf product, including 3,3,3-trifluoropropyne (TFPY), 1,2,3,3,3-pentafluoro-1-propene (1225ye), 3,3,3-trifluoropropene (1243zf), 1,3,3,3-tetrafluoropropene (1234ze), 1-chloro-1-fluoroethylene (1131a), vinyl chloride (1140), and 1-chloro-2-fluoroethylene (1131). These impurities are undesirable, and some of which are difficult to separate from 1234yf due to the impurities having boiling points which are close to that of 1234yf, and/or the possibility of one or more of the impurities forming azeotropic compositions with 1234yf.

What is needed is an effective method for separating unsaturated halogenated impurities from 1234yf.

SUMMARY OF THE DISCLOSURE

The present disclosure provides a method for removing unsaturated halogen impurities from 2,3,3,3-tetrafluoropropene (HFO-1234yf) of the type that may otherwise be difficult to separate from HFO-1234yf due to the impurities having boiling points which are close to that of HFO-1234yf and/or the potential of one or more of the impurities to form azeotropic mixtures with HFO-1234yf. A HFO-1234yf stream including unsaturated halogenated impurities is first passed through a caustic scrubber and is then passed through an acid scrubber. In the caustic scrubber and acidic scrubber, undesirable impurities are removed, in particular, 3,3,3-trifluoropropene (1243zf), 1-chloro-1-fluoroethylene (1131a), vinyl chloride (1140), and/or 1-chloro-2-fluoroethylene (1131).

In one form thereof, the disclosure provides a method for removing unsaturated halogenated impurities from 2,3,3,3-tetrafluoropropene (HFO-1234yf), including the steps of: providing a stream of 1234yf containing at least one impurity selected from the group consisting of 3,3,3-trifluoropropene (1243zf), 1-chloro-1-fluoroethylene (1131a), vinyl chloride (1140), 1-chloro-2-fluoroethylene (1131), and combinations thereof; and contacting the stream with an acidic scrubbing fluid in an acid scrubber.

In one embodiment, the at least one impurity includes 1-chloro-1-fluoroethylene (1131a) and, after the contacting step, an amount of 1131a in the stream is reduced by at least 5 wt. % relative to an amount of 1131a originally present in the stream. In another embodiment, the at least one impurity includes vinyl chloride (1140) and, after the contacting step, an amount of 1140 in the stream is reduced by at least 5 wt. % relative to an amount of 1140 originally present in the stream. In another embodiment, the at least one impurity includes 1-chloro-2-fluoroethylene (1131) and, after the contacting step, an amount of 1131 in the stream is reduced by at least 5 wt. % relative to an amount of 1131 originally present in the stream.

The acidic scrubbing fluid is sulfuric acid having a concentration between 88 wt. % and 99 wt. %, and at least one of the following conditions is present within the acid scrubber: a temperature between 0° C. and 70° C. and a contact time between the vapor stream and acidic scrubbing fluid of between 0.1 second and 200 seconds.

The method may further include the additional step, prior to the contacting step, of contacting the stream with a basic scrubbing fluid in a caustic scrubber. In one embodiment, the at least one impurity includes 3,3,3-trifluoropropene (1243zf) and, after the contacting step, an amount of 1243zf in the stream is reduced by at least 5 wt. % relative to an amount of 1243zf originally present in the stream.

In another form thereof, the present disclosure provides a method for removing unsaturated halogenated impurities from 2,3,3,3-tetrafluoropropene (HFO-1234yf), including the steps of: providing a stream of 1234yf containing at least one impurity selected from the group consisting of 3,3,3-trifluoropropene (1243zf), 1-chloro-1-fluoroethylene (1131a), vinyl chloride (1140), 1-chloro-2-fluoroethylene (1131), and combinations thereof; contacting the stream with a basic scrubbing fluid in a caustic scrubber; and thereafter, contacting the stream with an acidic scrubbing fluid in an acid scrubber.

In one embodiment, the at least one impurity includes 3,3,3-trifluoropropene (1243zf) and, after the contacting step, an amount of 1243zf in the stream is reduced by at least 5 wt. % relative to an amount of 1243zf originally present in the stream. In another embodiment, the at least one impurity includes 1-chloro-1-fluoroethylene (1131a) and, after the contacting step, an amount of 1131a in the stream is reduced by at least 5 wt. % relative to an amount of 1131a originally present in the stream. In another embodiment, the at least one impurity includes vinyl chloride (1140) and, after the contacting step, an amount of 1140 in the stream is reduced by at least 5 wt. % relative to an amount of 1140 originally present in the stream. In another embodiment, the at least one impurity includes 1-chloro-2-fluoroethylene (1131) and, after the contacting step, an amount of 1131 in the stream is reduced by at least 5 wt. % relative to an amount of 1131 originally present in the stream.

The acidic scrubbing fluid may be sulfuric acid having a concentration between 88 wt. % and 99 wt. %. At least one of the following conditions may be present within the acid scrubber: a temperature between 0° C. and 70° C.; and a contact time between the vapor stream and acidic scrubbing fluid of between 0.1 second and 200 seconds.

It is to be understood that both the foregoing general description and the following detailed description are exemplary and explanatory only and are not restrictive of the disclosure as claimed. Other embodiments will be apparent to those skilled in the art from consideration of the specification and practice of the disclosure disclosed herein.

BRIEF DESCRIPTION OF THE DRAWINGS

The above mentioned and other features of the disclosure, and the manner of attaining them, will become more apparent and the disclosure itself will be better understood by reference to the following description of embodiments of the disclosure taken in conjunction with the accompanying drawings.

FIG. 1 is a process flow diagram showing an exemplary process by which unsaturated halogenated impurities may be removed from 1234yf.

Although the drawings represent embodiments of various features and components according to the present disclosure, the drawings are not necessarily to scale and certain features may be exaggerated in order to better illustrate and explain the present disclosure. The exemplification set out herein illustrates an embodiment of the disclosure, and such exemplification is not to be construed as limiting the scope of the disclosure in any manner.

DETAILED DESCRIPTION

The present disclosure provides a method for removing unsaturated halogen impurities from 2,3,3,3-tetrafluoropropene (HFO-1234yf) of the type that may otherwise be difficult to separate from HFO-1234yf due to the impurities having boiling points which are close to that of HFO-1234yf and/or the potential of one or more of the impurities to form azeotropic mixtures with HFO-1234yf. A HFO-1234yf stream including unsaturated halogenated impurities is first passed through a caustic scrubber and is then passed through an acid scrubber. In the caustic scrubber and acid scrubber, undesirable impurities are removed, in particular, 3,3,3-trifluoropropene (1243zf), 1-chloro-1-fluoroethylene (1131a), vinyl chloride (1140), and/or 1-chloro-2-fluoroethylene (1131).

FIG. 1 is an exemplary process flow diagram for carrying out the present process. A vapor phase stream 10 is provided, which contains a crude HFO-1234yf product. Stream 10 may itself be a distillation vapor fraction obtained from a commercial production process for preparing HFO-1234yf, such as the process described in the background section above. In this connection, in addition to impurities, stream 10 may also include hydrogen chloride (HCl) and/or hydrogen fluoride (HF).

Stream 10 may contain various concentrations of HFO-1234yf, such as greater than 80 wt. %, greater than 90 wt. %, greater than 95 wt. %, or greater than 98 wt. %, for example, and the impurities may together comprise less than 20 wt. %, less than 10 wt. %, less than 5 wt. %, or less than 2 wt. %, for example.

The impurities in stream 10 may include one or more of 3,3,3-trifluoropropyne (TFPY), 1,2,3,3,3-pentafluoro-1-propene (1225ye), 3,3,3-trifluoropropene (1243zf), 1,3,3,3-tetrafluoropropene (1234ze), 1-chloro-1-fluoroethylene (1131a), vinyl chloride (1140), and 1-chloro-2-fluoroethylene (1131). In particular embodiments, the impurities in stream 10 may include one or more of 1243zf, 1131a, and 1140. The composition of stream 10 at any point in the present process, including amounts of HFO-1234yf and any of the impurities, may be determined by gas chromatography (GC).

In stream 10, TFPY may initially be present in an amount greater than 25 ppm and as high as 1000 ppm, as high as 500 ppm, or as high as 100 ppm, 1225ye may be initially present in an amount greater than 25 ppm and as high as 500 ppm, as high as 200 ppm, or as high as 100 ppm, 1243zf may be initially present in an amount greater than 25 ppm and as high as 500 ppm, as high as 200 ppm, or as high as 100 ppm, and/or 1234ze may be initially present in an amount greater than 25 ppm and as high as 5000 ppm, as high as 1000 ppm, or as high as 100 ppm.

1131a may be initially present in stream 10 in an amount greater than 25 ppm and as high as 500 ppm, as high as 200 ppm, or as high as 100 ppm, 1140 may be initially present in an amount greater than 25 ppm and as high as 500 ppm, as high as 200 ppm, or as high as 100 ppm, and/or 1131 may be initially present in an amount greater than 25 ppm and as high as 500 ppm, as high as 200 ppm, or as high as 100 ppm, for example.

Stream 10 is first directed to a caustic scrubber 12 where it is contacted with a caustic scrubbing fluid supplied from tank 14 via line 16, with tank 14 supplied with fresh caustic scrubbing fluid via line 18. The scrubbing fluid has a basic pH of greater than 7, for example greater than 10, and may include deionized water, distilled water, or tap water along with a basic agent to form a solution with a basic pH, such as sodium hydroxide (NaOH), potassium hydroxide (KOH), or calcium hydroxide ($Ca(OH)_2$), or any combination thereof, for example.

The concentration of the basic agent in the scrubbing fluid may be as little as 0.0004 wt. %, 0.04 wt. %, or 4 wt. %, or as great as 25 wt. %, 40 wt. %, or 65 wt. %, or may have a concentration in any range defined between any pair of the foregoing values, such as 0.0004 wt. % to 65 wt. %, 0.04 wt. % to 40 wt. %, or 4 wt. % to 25 wt. %, for example.

In caustic scrubber 12, the HCl and HF are neutralized by the scrubbing fluid to form water and metal halide salts, and it is believed that some of the impurities, including TPFY and 1243zf, may also react with the scrubbing fluid to form additional compounds which remain in the scrubbing fluid and are thereby separated from the HFO-1234yf stream. In this manner, the amount of TPFY and 1243zf impurities in the HFO-1234yf stream may be reduced. Spent caustic scrubbing fluid is returned from caustic scrubber 12 to tank 14 via line 20.

The temperature in caustic scrubber 12 may be as little as 0° C., 10° C., or 20° C., or may be as great as 30° C., 50° C., or 70° C., or may be within any range defined between any pair of the foregoing values, such as 0° C. to 70° C., 10° C. to 50° C., or 20° C. to 30° C., for example.

The pressure in caustic scrubber 12 may be as little as 0 psig, 3 psig, or 5 psig, or may be as great as 15 psig, 30 psig, or 50 psig, or may be within any range defined between any pair of the foregoing values, such as 0 psig to 50 psig, 3 psig to 30 psig, or 5 psig to 15 psig, for example, though the pressure in caustic scrubber 12 may vary, and it is not believed to be an important variable in the present process.

The contact time between the HFO-1234yf stream and the scrubbing fluid in caustic scrubber 12 may be as little as 0.1 second, 1 second, or 5 seconds, or may be as great as 50 seconds, 100 seconds, or 200 seconds, or more, or may be within any range defined between any pair of the foregoing values, such as 0.1 second to 200 seconds, 1 second to 100 seconds, or 5 seconds to 50 seconds, for example.

Thereafter, the HFO-1234yf vapor stream, also including water vapor, exits caustic scrubber 12 through line 22 and passes through a heat exchanger or pre-cooler 24 to cool the vapor. Condensed water vapor may be returned to tank 14 via line 26. Otherwise, the stream is directed via line 22 to caustic scrubber knock-out pot 28 where entrained scrubbing fluid (caustic solution) is removed via line 30 to return to scrubbing fluid tank 14. Spent scrubbing fluid may be removed from tank 14 via line 21.

Vapor, including HFO-1234yf and remaining impurities, is then directed from knock-out pot 28 via line 32 to acid scrubber 34, where the vapor stream is contacted with an acidic scrubbing fluid. The acid may be a sulfuric acid ($H_2SO_4$) solution having a concentration as little as 88 wt. %, 90 wt. %, or 92 wt. %, or as great as 96 wt. %, 98 wt. %, or 99 wt. %, or may have a concentration in any range defined between any pair of the foregoing values, such as 88 wt. % to 99 wt. %, 90 wt. % to 98 wt. %, or 92 wt. % to 96 wt. %, for example.

Acid scrubber 34 is supplied with acidic scrubbing fluid from tank 36 via line 38, and it is believed that the scrubbing fluid may also react with 1131a, 1140, and 1131 impurities to form products which are carried away the scrubbing fluid and thereby separated from the HFO-1234yf stream. In this manner, the amounts of 1131a, 1140, and 1131 impurities in the HFO-1234yf stream may be reduced. Spend scrubbing fluid from scrubber 34 may return to tank 36 via line 40. Tank 36 may be resupplied with fresh scrubbing fluid via line 42 and spent scrubbing fluid may be removed via line 44.

The temperature in acid scrubber 34 may be as little as 0° C., 10° C., or 20° C., or may be as great as 30° C., 50° C., or 70° C., or may be within any range defined between any pair of the foregoing values, such as 0° C. to 70° C., 10° C. to 50° C., or 20° C. to 30° C., for example.

The pressure in acid scrubber 34 may be as little as 0 psig, 3 psig, or 5 psig, or may be as great as 15 psig, 30 psig, or 50 psig, or may be within any range defined between any pair of the foregoing values, such as 0 psig to 50 psig, 3 psig to 30 psig, or 5 psig to 15 psig, for example, though the pressure in acid scrubber 34 may vary, and it is not believed to be an important variable in the present process.

The contact time between the HFO-1234yf vapor stream and the scrubbing fluid in the acid scrubber 34 may be as little as 0.1 second, 1 second, or 5 seconds, or may be as great as 50 seconds, 100 seconds, or 200 seconds, or more, or may be within any range defined between any pair of the foregoing values, such as 0.1 second to 200 seconds, 1 second to 100 seconds, or 5 seconds to 50 seconds, for example.

The HFO-1234yf stream is removed from acid scrubber via line 46 and may be passed through a drier 48 to remove any residual moisture. Drier 48 may include a suitable drying agent such as molecular sieves. Thereafter, the stream may be passed through a filter 50 before being directed to further unit operations, such as additional purifying steps, for example.

The present process may be effective to reduce the amount of 1243zf in the HFO-1234yf stream. In some embodiments of the present disclosure, the amount of 1243zf impurity in the 1234yf stream is reduced at least by 5 wt. % relative to the amount of 1243zf impurity originally present in the 1234yf stream, or the amount of 1243zf impurity may be reduced at least by 10 wt. % relative to the amount of 1243zf impurity originally present in the 1234yf stream.

The present process may be effective to reduce the amount of 1131a in the HFO-1234yf stream. In some embodiments of the present disclosure, the amount of 1131a impurity in the 1234yf stream is reduced at least by 5 wt. % relative to the amount of 1131a impurity originally present in the 1234yf stream, the amount of 1131a impurity may be reduced at least by 10 wt. % relative to the amount of 1131a impurity originally present in the 1234yf stream, or the amount of 1131a impurity may be reduced at least by 20 wt. % relative to the amount of 1131a impurity originally present in the 1234yf stream.

The present process may be effective to reduce the amount of 1140 in the HFO-1234yf stream. In some embodiments of the present disclosure, the amount of 1140 impurity in the 1234yf stream is reduced at least by 5 wt. % relative to the amount of 1140 impurity originally present in the 1234yf stream, the amount of 1140 impurity may be reduced at least by 10 wt. % relative to the amount of 1140 impurity originally present in the 1234yf stream, or the amount of 1140 impurity may be reduced at least by 20 wt. % relative to the amount of 1140 impurity originally present in the 1234yf stream.

The present process may be effective to reduce the amount of 1131 in the HFO-1234yf stream. In some embodiments of the present disclosure, the amount of 1131 impurity in the 1234yf stream is reduced at least by 5 wt. % relative to the amount of 1131 impurity originally present in the 1234yf stream, the amount of 1131 impurity may be reduced at least by 10 wt. % relative to the amount of 1131 impurity originally present in the 1234yf stream, or the amount of 1131 impurity may be reduced at least by 20 wt. % relative to the amount of 1131 impurity originally present in the 1234yf stream.

EXAMPLES

Example 1

A 20" PFA test tube with ½" OD was filled with 26 ml of 1.0 wt. % NaOH solution. At ambient temperature (20-30° C.), an organic stream containing 99.96% 1234yf, 121 ppm 1243zf, 88 ppm 1131a, and 101 ppm 1140 was fed into the test tube from the bottom of the test tube via a mass flowmeter and controller, a check valve and a gas sparger, and the organic vapor at the outlet of the test tube was periodically sampled and analyzed by GC. The flow rate of the organic stream was controlled at 20.9 g/h which gave a contact time of 28 seconds between 1.0 wt % NaOH and organic stream. During 29 hours test, the organic stream at the outlet contained, on average, 99.86% 1234yf, 104 ppm 1243zf, 92 ppm 1131a, and 98 ppm 1140, respectively. 1243zf concentration in the outlet organic stream was reduced by 13.5%.

Example 2

A 20" PFA test tube with ½" OD was filled with 26 ml of 4.0 wt. % NaOH solution. At ambient temperature (20-30°

C.), an organic stream containing 99.96% 1234yf, 121 ppm 1243zf, 88 ppm 1131a, and 101 ppm 1140 was fed into the test tube from the bottom of the test tube via a mass flowmeter and controller, a check valve and a gas sparger, and the organic vapor at the outlet of the test tube was periodically sampled and analyzed by GC. The flow rate of the organic stream was controlled at 20.9 g/h which gave a contact time of 28 seconds between 4.0 wt % NaOH and organic stream. During 19 hours test, the organic stream at the outlet contained, on average, 99.92% 1234yf, 106 ppm 1243zf, 93 ppm 1131a, and 99 ppm 1140, respectively. 1243zf concentration in the outlet organic stream was reduced by 11.9%.

Example 3

A 20" PFA test tube with ½" OD was filled with 26 ml of $H_2SO_4$ (95-98%, Sigma-Aldrich). At ambient temperature (20-30° C.), an organic stream containing 1234yf, 1243zf, 1131a, and 1140 was fed into the test tube from the bottom of the test tube via a mass flowmeter and controller, a check valve and a gas sparger, and the organic vapor at the inlet and outlet of the test tube were periodically sampled and analyzed by GC. The flow rate of the organic stream was controlled at 20.9 g/h which gave a contact time of 28 seconds between $H_2SO_4$ and organic stream. During 31 hours test, the organic stream at the inlet contained, on average, 99.97% 1234yf, 110 ppm 1243zf, 91 ppm 1131a, and 98 ppm 1140, respectively. The organic stream at the outlet contained, on average, 99.96% 1234yf, 109 ppm 1243zf, 55 ppm 1131a, and 64 ppm 1140, respectively. 40.3% and 34.8% reductions in 1131a and 1140 concentrations, respectively, in the outlet organic stream were observed.

Example 4

A 20" PFA test tube with ½" OD was filled with 26 ml of $H_2SO_4$ (95-98%, Sigma-Aldrich). At ambient temperature (20-30° C.), an organic stream containing 1234yf, 1243zf, 1131a, and 1140 was fed into the test tube from the bottom of the test tube via a mass flowmeter and controller, a check valve and a gas sparger, and the organic vapor at the inlet and outlet of the test tube were periodically sampled and analyzed by GC. The flow rate of the organic stream was controlled at 41.8 g/h which gave a contact time of 14 seconds between $H_2SO_4$ and organic stream. During 29 hours test, the organic stream at the inlet contained, on average, 99.97% 1234yf, 108 ppm 1243zf, 96 ppm 1131a, and 103 ppm 1140, respectively. The organic stream at the outlet contained, on average, 99.97% 1234yf, 109 ppm 1243zf, 75 ppm 1131a, and 81 ppm 1140, respectively. 21.4% and 21.5% reductions in 1131a and 1140 concentrations, respectively, in the outlet organic stream were observed.

Example 5

A 20" PFA test tube with ½" OD was filled with 26 ml of $H_2SO_4$ (95-98%, Sigma-Aldrich). At ambient temperature (20-30° C.), an organic stream containing 1234yf, 1243zf, 1131a, and 1140 was fed into the test tube from the bottom of the test tube via a mass flowmeter and controller, a check valve and a gas sparger, and the organic vapor at the inlet and outlet of the test tube were periodically sampled and analyzed by GC. The flow rate of the organic stream was controlled at 20.9 g/h which gave a contact time of 28 seconds between $H_2SO_4$ and organic stream. During 23 hours test, the organic stream at the inlet contained, in average, 99.98% 1234yf, 55 ppm 1243zf, 37 ppm 1131a, and 43 ppm 1140, respectively. The organic stream at the outlet contained, on average, 99.99% 1234yf, 55 ppm 1243zf, 22 ppm 1131a, and 28 ppm 1140, respectively. 41.1% and 36.5% reductions in 1131a and 1140 concentrations, respectively, in the outlet organic stream were observed.

Example 6

A 20" PFA test tube with ½" OD was filled with 26 ml of $H_2SO_4$ (95-98%, Sigma-Aldrich). At ambient temperature (20-30° C.), an organic stream containing 1234yf, 1243zf, 1131a, and 1140 was fed into the test tube from the bottom of the test tube via a mass flowmeter and controller, a check valve and a gas sparger, and the organic vapor at the inlet and outlet of the test tube were periodically sampled and analyzed by GC. The flow rate of the organic stream was controlled at 41.8 g/h which gave a contact time of 14 seconds between $H_2SO_4$ and organic stream. During 18.5 hours test, the organic stream at the inlet contained, in average, 99.98% 1234yf, 57 ppm 1243zf, 37 ppm 1131a, and 44 ppm 1140, respectively. The organic stream at the outlet contained, on average, 99.99% 1234yf, 58 ppm 1243zf, 25 ppm 1131a, and 31 ppm 1140, respectively. 31.5% and 29.1% reductions in 1131a and 1140 concentrations, respectively, in the outlet organic stream were observed.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances that fall within the scope of the appended claims.

The invention claimed is:

1. A method for removing unsaturated halogenated impurities from 2,3,3,3-tetrafluoropropene (HFO-1234yf), comprising the steps of:
   providing a stream of 1234yf containing at least one impurity selected from the group consisting of 3,3,3-trifluoropropene (1243zf), 1-chloro-1-fluoroethylene (1131a), vinyl chloride (1140), 1-chloro-2-fluoroethylene (1131), and combinations thereof; and
   contacting the stream with an acidic scrubbing fluid in an acid scrubber.

2. The method of claim 1, wherein the at least one impurity includes 1-chloro-1-fluoroethylene (1131a) and, after said contacting step, an amount of 1131a in the stream is reduced by at least 5 wt. % relative to an amount of 1131a originally present in the stream.

3. The method of claim 1, wherein the at least one impurity includes vinyl chloride (1140) and, after said contacting step, an amount of 1140 in the stream is reduced by at least 5 wt. % relative to an amount of 1140 originally present in the stream.

4. The method of claim 1, wherein the at least one impurity includes 1-chloro-2-fluoroethylene (1131) and, after said contacting step, an amount of 1131 in the stream is reduced by at least 5 wt. % relative to an amount of 1131 originally present in the stream.

5. The method of claim 1, wherein the acidic scrubbing fluid is sulfuric acid having a concentration between 88 wt. % and 99 wt. %.

6. The method of claim 1, wherein at least one of the following conditions are present within the acid scrubber:
a temperature between 0° C. and 70° C.; and
a contact time between the vapor stream and acidic scrubbing fluid of between 0.1 second and 200 seconds.

7. The method of claim 1, further comprising the additional step, prior to said contacting step, of contacting the stream with a basic scrubbing fluid in a caustic scrubber.

8. The method of claim 7, wherein the at least one impurity includes 3,3,3-trifluoropropene (1243zf) and, after said contacting step, an amount of 1243zf in the stream is reduced by at least 5 wt. % relative to an amount of 1243zf originally present in the stream.

9. A method for removing unsaturated halogenated impurities from 2,3,3,3-tetrafluoropropene (HFO-1234yf), comprising the steps of:
providing a stream of 1234yf containing at least one impurity selected from the group consisting of 3,3,3-trifluoropropene (1243zf), 1-chloro-1-fluoroethylene (1131a), vinyl chloride (1140), 1-chloro-2-fluoroethylene (1131), and combinations thereof;
contacting the stream with a basic scrubbing fluid in a caustic scrubber; and
thereafter, contacting the stream with an acidic scrubbing fluid in an acid scrubber.

10. The method of claim 9, wherein the at least one impurity includes 3,3,3-trifluoropropene (1243zf) and, after said contacting step, an amount of 1243zf in the stream is reduced by at least 5 wt. % relative to an amount of 1243zf originally present in the stream.

11. The method of claim 9, wherein the at least one impurity includes 1-chloro-1-fluoroethylene (1131a) and, after said contacting step, an amount of 1131a in the stream is reduced by at least 5 wt. % relative to an amount of 1131a originally present in the stream.

12. The method of claim 9, wherein the at least one impurity includes vinyl chloride (1140) and, after said contacting step, an amount of 1140 in the stream is reduced by at least 5 wt. % relative to an amount of 1140 originally present in the stream.

13. The method of claim 9, wherein the at least one impurity includes 1-chloro-2-fluoroethylene (1131) and, after said contacting step, an amount of 1131 in the stream is reduced by at least 5 wt. % relative to an amount of 1131 originally present in the stream.

14. The method of claim 9, wherein the acidic scrubbing fluid is sulfuric acid having a concentration between 88 wt. % and 99 wt. %.

15. The method of claim 9, wherein at least one of the following conditions are present within the acid scrubber:
a temperature between 0° C. and 70° C.; and
a contact time between the vapor stream and acidic scrubbing fluid of between 0.1 second and 200 seconds.

16. The method of claim 1, wherein the following conditions are present within the acid scrubber:
a temperature between 20° C. and 30° C.; and
a contact time between the vapor stream and acidic scrubbing fluid of between 5 seconds and 50 seconds.

17. The method of claim 9, wherein the following conditions are present within the acid scrubber:
a temperature between 20° C. and 30° C.; and
a contact time between the vapor stream and acidic scrubbing fluid of between 5 seconds and 50 seconds.

* * * * *